United States Patent [19]
Hanson

[11] Patent Number: 5,456,599
[45] Date of Patent: Oct. 10, 1995

[54] ORTHODONTIC ARCH WIRES AND BRACKETS

[75] Inventor: G. Herbert Hanson, Hamilton, Canada

[73] Assignee: Hamilton Ortho Inc., Hamilton, Canada

[21] Appl. No.: 852,861

[22] Filed: Mar. 17, 1992

[51] Int. Cl.⁶ ............................................. A61C 3/00
[52] U.S. Cl. ..................................... 433/8; 433/20
[58] Field of Search ....................... 433/8, 9, 10, 11, 433/12, 13, 14, 15, 16, 17, 18, 19, 20

[56] References Cited

U.S. PATENT DOCUMENTS

| | | | |
|---|---|---|---|
| 3,605,233 | 9/1971 | Rosiello | 433/8 |
| 4,050,156 | 9/1977 | Chasanoff et al. | 433/20 |
| 4,219,617 | 8/1980 | Wallshein | 433/8 |
| 4,850,865 | 7/1989 | Napolitano | 433/20 |
| 5,154,607 | 10/1992 | Hanson | 433/8 |
| 5,174,753 | 12/1992 | Wool | 433/20 |
| 5,174,754 | 12/1992 | Meritt | 433/8 |

Primary Examiner—John J. Wilson
Attorney, Agent, or Firm—Rogers & Scott

[57] ABSTRACT

An arch wire of T-shape cross section in the gingival occlusal transverse plane so as to have a labial lingual extending foot and a gingival occlusal extending crossbar is operative with a bracket having a mesial distal extending arch wire slot. The crossbar is urged against the bracket body by a ligature, usually an elastic ligation loop, until its lingual surfaces, which preferably are flat and coplanar, are in full butting engagement with the slot bordering portions of the bracket labial surface, which preferably are also flat and coplanar. At this time the foot is fully inserted in the slot and the optimum relative position and attitude of the bracket and the wire is determined for both tipping and rotation by this butting engagement. The function of the foot is primarily to guide the wire into this engagement and it can therefore fit with good clearance in the slot. The wire is usually used toward the end of the procedure after initial corrections and movements have been produced using round cross section wires. This replaces the prior art system of square or rectangular wires fitting in a rectangular slot. The labial slot surface is concave, usually semi-circular, so that it cooperates effectively with the round cross section wires used in the initial stages.

44 Claims, 6 Drawing Sheets

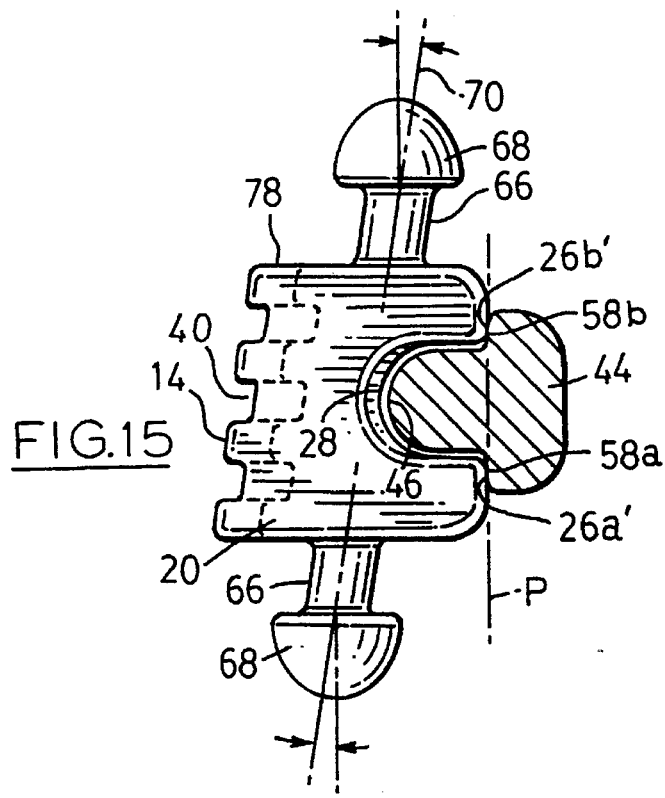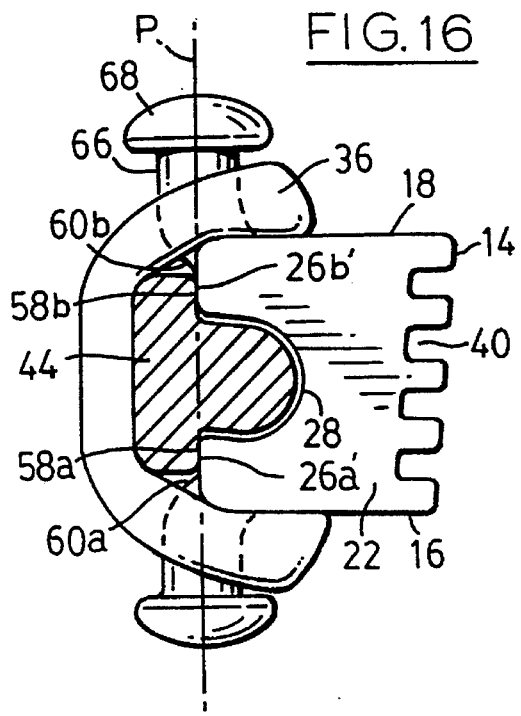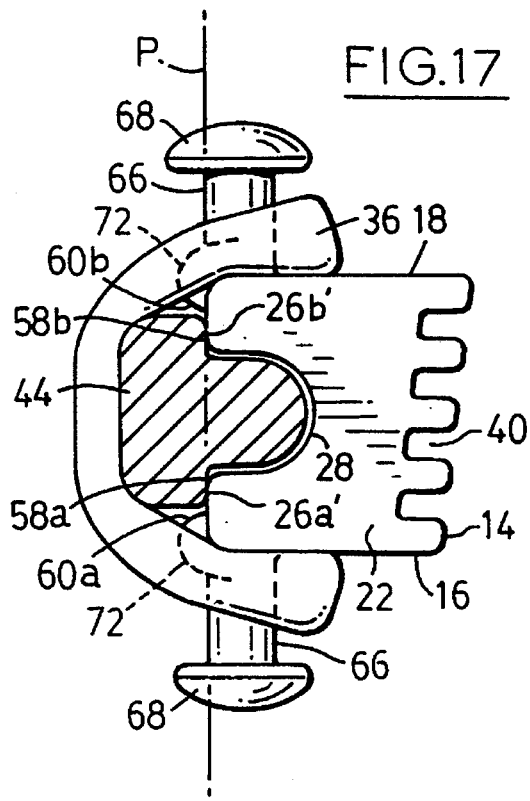

ORTHODONTIC ARCH WIRES AND BRACKETS

FIELD OF THE INVENTION

This invention is concerned with improvements in orthodontic arch wires that are used in orthodontic procedures to connect together a plurality of orthodontic brackets attached to the teeth, the wires being operative to rotate and tip the brackets, thereby moving the teeth to a desired conformation set by the arch wire. The invention is also concerned with new orthodontic brackets for use in combination with such arch wires.

REVIEW OF THE PRIOR ART

The majority of orthodontic procedures now employ a plurality of brackets that are attached to respective teeth, usually by cementing them to the teeth, together with one or more arch wires, so called because they are preformed to an optimum arch shape corresponding to the desired conformation of the teeth. The wires are engaged in cooperating rectangular cross section slots in the brackets and attached to the brackets by ligating wires, or by ligating elastomeric loops, or by self-ligating springs that are part of the bracket. An example of a bracket employing a self-ligating spring is that disclosed and claimed in my U.S. Pat. Nos. 4,248,588 and 4,492,573.

In a typical procedure the first arch wire employed is an "undersize" multistrand very springy wire of circular transverse cross section, and of very low load deflection rate, that is a very loose fit in the bracket slots, so that the correcting forces it can apply to the brackets, and thus to the teeth, are correspondingly small, as is desired to avoid the possibility of tissue damage and/or root resorbtion. After several weeks the corrective effect of this undersize wire decreases to an inefficient value, and it is replaced with a less springy wire of larger diameter; this successive replacement is continued until the wire in use is of the largest diameter that can be inserted in the slot while not producing excessive sliding friction between the wire and the bracket that would inhibit any desired mesial or distal corrective sliding movement of the brackets along the wire. This arch wire of largest diameter may still be of inherently springy material, and can then be replaced by wires of progressively increasing stiffness. Alternatively, the diameter and the inherent stiffness may be increased together. At some stage the round cross section wires are usually replaced by rectangular cross section wires which cooperate with the rectangular cross section slots to give greater control of tipping (commonly called "torquing") of the teeth about the mesial distal slot axis. During some stages of the procedure the brackets may be connected by tension springs to produce the desired retraction or protraction tooth movements.

The choice of the dimensions and cross-sections of the rectangular bracket slot and its co-operating rectangular wires has presented a difficult problem, which is exacerbated by the fact that they are used toward the end of the procedure when substantial correction has already been achieved. Ideally the wire is a very close fit in the slot, so that the bracket is held at the end of the procedure as close as possible to its optimum attitude relative to rotation about the mesial distal slot axis, but such a close fit makes it very difficult to insert the wire in the slots, especially if it must be bent or twisted to engage it in the immediately adjacent slots. In addition, the close fitting wire may produce a corresponding counter torque on the adjacent already optimized brackets that moves them away from those optimum positions. Typically if the gingival occlusal dimension of a square or rectangular arch wire is 0.5 mm (0.020 in.), then the corresponding dimension of the bracket slot is 0.55 mm (0.022 in.), corresponding to a tolerance of ±5%. It is also known however to use wires that are a nominal 0.50 mm (0.020 in.), i.e. that are actually 0.48 mm (0.0192 in.), in a bracket slot is also a nominal 0.55 mm (0.022 in.), actually 0.575 mm (0.023 in.) for a tolerance of about ±10%.

It is the desire of both orthodontists and their patients that the procedures should proceed as rapidly as possible, with the proviso as indicated above that the forces employed are not such as to cause damage to the tissue or the teeth. To this end there have been a number of prior suggestions of arch wires of special cross section, which will cooperate particularly effectively to this end with brackets having rectangular and other cross section slots of appropriate size, and an example of such a special cross section wire and slot is described in my U.S. Pat. No. 4,248,588 and shown in FIG. 11 thereof.

It is also a desire to provide orthodontic devices, such as arch wires and their brackets, that permit and facilitate the use of relatively light correcting forces during all the stages of an orthodontic procedure, especially since it is found that the appropriate use of these light correcting forces can result in corrective procedures that are at least as fast, and can even be significantly faster, than prior procedures using heavier forces, while providing the above described reduced risk of damage to teeth and supporting tissues.

It is a further desire to provide brackets that are as small as possible, so as to be cosmetically more attractive, and so as to reduce the possibility of mechanical interference with adjacent and opposing teeth and brackets.

SUMMARY OF THE INVENTION

It is the principal object of the invention to provide a new arch wire for use in combination with an orthodontic bracket.

It is another object to provide a new combination of such an arch wire and a bracket that are used in combination with one another.

It is a further object to provide a new combination of such an arch wire, a bracket and ligature means therefor that are used in combination with one another.

In accordance with the invention there is provided an orthodontic arch wire for use in combination with an orthodontic bracket comprising a bracket body having the usual labial, lingual, gingival, occlusal, mesial and distal surfaces, and having a mesial distal extending arch wire slot opening at the bracket labial surface, the bracket labial surface being divided by the slot to have two labial slot border surface parts on respective sides of the slot.

The arch wire is of T-shape cross section in a gingival occlusal transverse plane, thus comprising a labial lingual extending foot portion and a gingival occlusal extending crossbar portion, the latter having two spaced lingual surface parts that have respective mesial distal extending junctions with the gingival and occlusal surfaces of the foot portion. The gingival occlusal height of the foot portion is smaller than the corresponding height of the bracket slot for the foot portion to be insertable into the bracket slot with clearance between the foot portion gingival and occlusal surfaces and the corresponding adjacent slot gingival and occlusal surfaces, while the lingual surface of the foot portion is convex toward the lingual and is rounded in the gingival occlusal transverse plane. The gingival occlusal height of the crossbar portion is greater than the corresponding height of the bracket slot, so that the two spaced crossbar lingual surface parts butt against the two respective bracket labial slot border surface parts when the foot portion is fully inserted into the slot and thereby establish the position and the attitude of the wire and the bracket relative to one another.

Also in accordance with the invention there is provided the combination of such an arch wire with an orthodontic bracket cooperating therewith. When the bracket and the arch wire are not in optimum position and attitude relative to one another the foot portion protrudes into the slot to maintain the bracket and the arch wire in cooperative engagement with one another, and movement of the foot portion into the slot guides the bracket and the arch wire toward the optimum position and attitude, the optimum position and attitude being established by the butting engagement of both of the crossbar lingual surface parts with both of the respective bracket labial slot border surface parts.

The combination may further comprise ligating means on the bracket body for engagement with the labial face of the arch wire and to urge the arch wire lingually to move the foot portion fully into the slot for said butting engagement of both of the crossbar lingual surface parts with both of the respective bracket labial slot border surface parts.

The lingual surface of the arch wire foot portion may be semi-circular about a mesial distal axis in the gingival occlusal transverse plane.

The slot lingual surface may be concave toward the labial in a gingival occlusal transverse plane, and preferably the surface also is semi-circular about a mesial distal axis in the gingival occlusal transverse plane.

The two arch wire crossbar portion lingual surface parts may be coplanar and both have right angle junctions with the respective gingival and occlusal surfaces of the foot portion, the two bracket labial slot border surface parts that are butted by the crossbar portion lingual surface parts also being flat and coplanar with one another. Alternatively, the said two arch wire surface parts both have obtuse angle junctions with the respective gingival and occlusal surfaces of the foot portion, and the two slot border surface parts that are butted by them are inclined labially from their junctions with the slot edges, so that they are also obtuse angled. In another alternative the said two arch wire surface parts both have acute angle junctions with the respective gingival and occlusal surfaces of the foot portion, and the two slot border surface parts that are butted thereby are inclined lingually from their junctions with the slot edges, so that the said junctions are also acute angled.

The butting arch wire and bracket surface parts may each or both have a mirror surface finish of roughness not more than 0.75 micrometer (30 microinch), or they may each or both have thereon a coating of a lower friction material, with the intention of reducing the sliding friction between them.

The bracket body may be provided beyond the respective labial slot border labial surface parts with two labially gingivally and labially occlusally facing mesially distally extending stop surfaces on each side of the slot protruding labially beyond the respective labial slot border surface parts, a respective stop surface being engaged by the arch wire upon a predetermined relative rotation of the bracket and the arch wire from the optimum attitude about a mesial distal extending axis.

In some embodiments the slot mesially and distally extending gingival and occlusal surfaces may diverge away from one another from the lingual toward the labial.

DESCRIPTION OF THE DRAWINGS

Particular preferred embodiments of the invention will now be described, by way of example, with reference to the accompanying diagrammatic drawings, wherein:

FIGS. 16–17 are respective end elevations of brackets which are still further embodiments of the invention, also employing headed posts.

DESCRIPTION OF THE PREFERRED EMBODIMENTS

Figure 1:
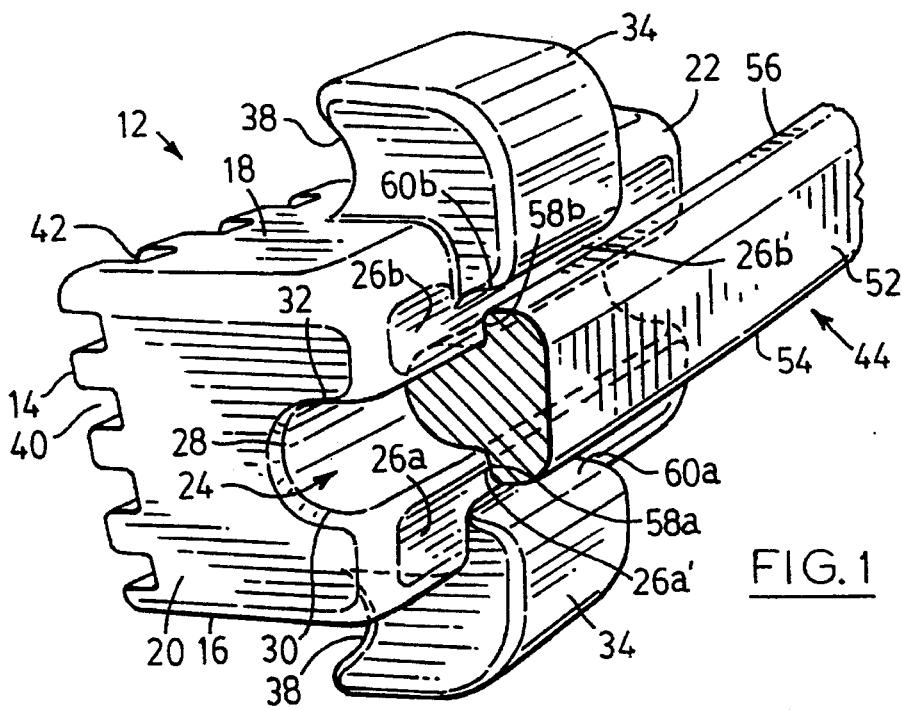
FIG. 1 is a perspective view of a bracket that is a first embodiment of the invention, the bracket having a portion of an arch wire of the invention fully inserted into the bracket arch wire slot, the figure therefore illustrating the dispositions of the bracket and arch wire relative to one another when the latter is attached to a tooth that has been moved by the arch wire and bracket combination to its desired "optimized" attitude.

For convenience and simplicity in description the embodiments are illustrated and described herein and claimed in the appended claims as they would be used in the upper central incisor region of a patient's mouth and in the conventional so-called labial technique, in which the brackets are attached to the labial surfaces of the teeth. The brackets and arch wires of the invention are equally usable in the so-called lingual technique, in which the brackets are attached to the lingual surfaces of the teeth so that they are concealed from view as much as possible.

The bracket of FIG. 1–4 consists of a bracket body 12 having lingual, gingival, occlusal, mesial and distal surfaces 14, 16, 18, 20 and 22 respectively. The body is provided with a mesial-distal extending arch wire slot 24 opening to the labial surface of the body, which is divided by the slot into two coplanar parallel labial surface parts 26a and 26b. The slot has lingual, gingival and occlusal surfaces 28, 30 and 32 respectively, the two surfaces 30 and 32 being parallel to one another, while the lingual surface 28 is semi-circular in a transverse gingival occlusal extending plane. As is well known to those skilled in this art it is usual in orthodontic bracket manufacture to avoid sharp edge junctions between the various surfaces, and they therefore merge smoothly with one another without a definite junction between them being apparent.

Two opposed tie wings 34 for the reception of a ligation tie wire, or more usually an elastic ligature loop such as an elastomeric loop 36, protrude from the bracket gingival and occlusal surfaces and the respective labial surface parts centrally between the mesial and distal ends; the mesial distal width of the tie wings usually is about 30–50% of the total body width, and preferably is about 40%. The lingual surfaces 38 of the tie wings are undercut for better retention of the ligature and are spaced from the body lingual surface a sufficient distance to provide adequate room for the ligature to be passed between them and the tooth to which the bracket is attached. The tie wings protrude from the labial surface parts 26a and 26b at locations which are spaced from the edges of the slot, i.e. from the junctions of these surface parts 26a and 26b with the slot surfaces 30 and 32, so as to form adjacent to these slot edges respective lingual surface portions 26a' and 26b' that are coplanar in a plane P (FIG. 2) with the respective surface parts 26a and 26b, and that extend across the full width of the bracket body.

The bracket body lingual surface 14 is provided with a first plurality of parallel mesial distal extending slots 40, and a second plurality of parallel gingival-occlusal extending slots 42 that cross the slots 40 to provide recesses for the reception of cement by which the bracket is attached to a tooth. The brackets of the invention are employed in a technique with which each bracket is attached to its respective tooth in an attitude such that, as each arch wire attempts to return to its preformed arch shape, each tooth is moved toward its desired optimized position and attitude. To achieve this all of the torque requirements (rotation about a mesial distal axis), angulation requirements (rotation about a labial lingual axis), and first order pre-adjustments, are obtained by suitable shaping of the bracket bases, particularly of their lingual surfaces and variation of their thicknesses, so that all of the labial faces are aligned when the teeth are in their optimum attitude and rotational position. In practice the first-used arch wires will be unable to achieve this, and it is desired that it be achieved before the last wire is used, so that the principal function of that wire will be the final tipping and rotation of the teeth which, as described above, has previously usually been achieved by use of a rectangular cross section wire operating in a rectangular cross section slot.

The lingual face 14 is curved in its respective gingival occlusal extending plane so as to conform as closely as possible to the curvature of the labial surface of the tooth to which it is to be attached, this objective being subject to the consideration that it is not practical in commercial practice to provide for every variation in tooth contour that is encountered, and some tolerance is provided by the gap-filling capability of the cements used to fix the brackets to the teeth. In this embodiment the surface 14 is inclined at an angle x (FIG. 2) to a plane Q parallel to the plane P, so that with the bracket illustrated the mesial and distal surfaces taper with decreasing width from the occlusal toward the gingival. All of these pre-adjustments, together with the position and attitude in which the brackets are attached to their respective teeth, have the objective that at the conclusion of the corrective procedure the labial surface parts and portions 26a, 26b, 26a' and 26b' will all lie in the optimal plane P. As will become apparent from the description below, the labial surface parts and portions and the slot lingual surface 28 can also be curved to conform as closely as practicable to the optimized arch wire shape; such curvature is not usually needed with the brackets attached to the bicuspids and molars since the corresponding parts of the arch wire are almost straight.

Figure 2:
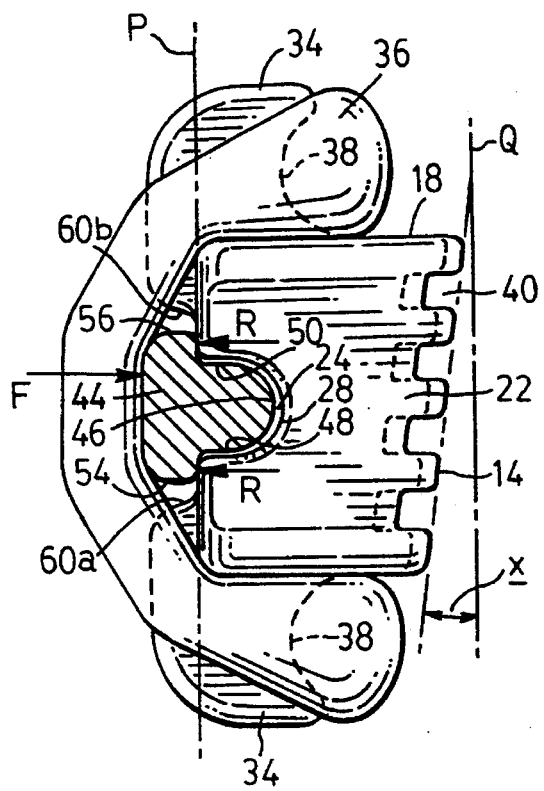
FIG. 2 is an end elevation from the mesial or distal of the bracket and arch wire of FIG. 1, the wire being shown in cross section.

An orthodontic arch wire 44 of the invention is of T-shape cross section in a gingival occlusal transverse plane, the cross section therefore having a labial lingual extending foot portion and a gingival occlusal extending crossbar portion. The foot portion has lingual, gingival and occlusal surfaces 46, 48 and 50 respectively, while the crossbar portion has labial, gingival and occlusal surfaces 52, 54 and 56 respectively. The crossbar portion also has two lingual surface parts 58a and 58b that are coplanar in a plane P' (FIG. 6) and have respective mesial distal extending junctions with the gingival and occlusal surfaces 48 and 50 of the foot portion. When, as illustrated by FIGS. 1 and 2, the bracket is in its fully optimized position and attitude, the foot portion is fully inserted into the arch wire slot. There is a relatively generous clearance between the arch wire surfaces and the slot surfaces, although for clarity of illustration the Figures are not shown to scale. In this fully optimized position both lingual surface parts 58a and 58b of the wire are in respective butting engagement with both of the bracket labial surface portions 26a' and 26b' and ideally this butting contact extends over the full width of the bracket. The force applied by the ligature loop 36 (indicated by arrow F in FIG. 2) is met equally by the gingivally occlusally spaced reaction forces (arrows R in FIG. 2) between the arch wire lingual surface parts 58a and 58b and the bracket labial surface parts 26a and 26b, more specifically the portions 26a' and 26b'.

Figure 3:
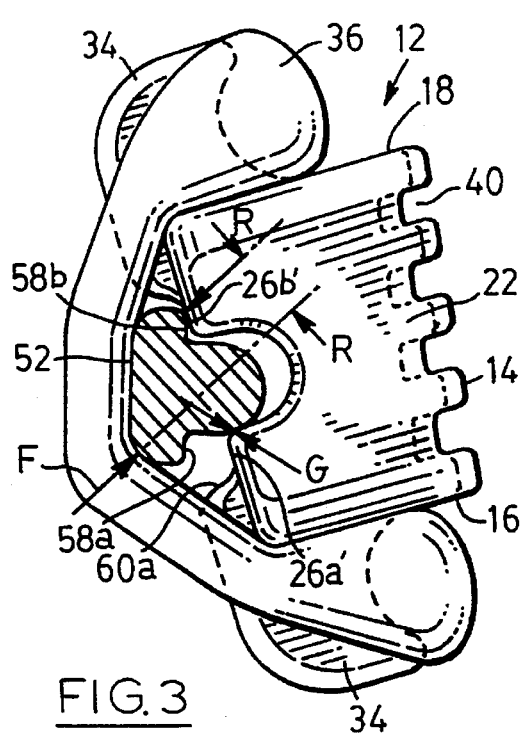
FIG. 3 is an end elevation similar to FIG. 2 and showing typical relative dispositions of the arch wire and bracket when the latter is attached to a tooth that is in a non-optimized attitude.
Figure 4:
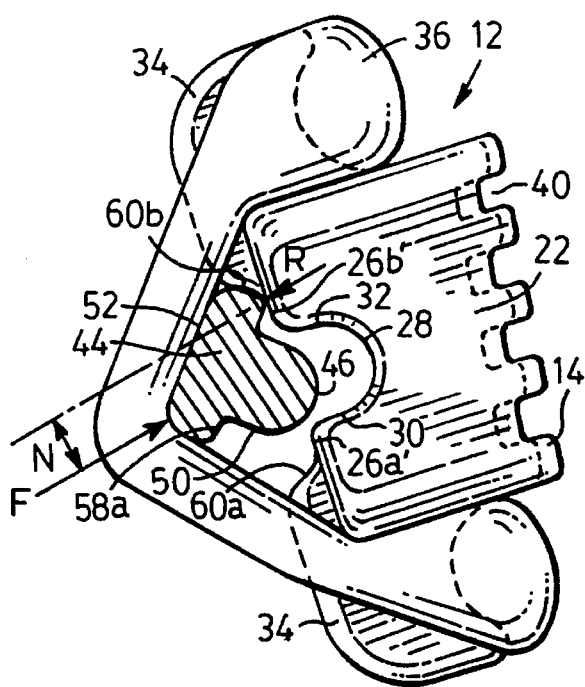
FIG. 4 is an end elevation similar to FIGS. 2 and 3 and showing the bracket and arch wire in a relatively extreme non-optimized attitude.

In any non-optimized bracket position, for example in the relatively tipped positions illustrated by FIGS. 3 and 4, the wire foot is no longer fully inserted in the bracket slot. FIG. 3 illustrates the case where there is still butting contact at points indicated by arrows G between one of the arch wire lingual surface parts and its corresponding bracket labial surface portion (part 58a and portion 26a' in this illustration). Moreover, this butting contact may only occur across part of the bracket body width because of rotation of the tooth and bracket about a gingival occlusal axis out of the optimum position. FIG. 4 illustrates the case where the tipping is such that the wire crossbar occlusal surface 56 has engaged a mesially distally extending tie wing stop surface portion 60a that faces both labially and gingivally and, in this embodiment, is also shaped to conform to the surface 56 and receive it snugly, so that the wire and stop surfaces tend to stay in abutting contact even if relative rotation beyond that illustrated is present. This butting contact between the mutually conforming surfaces 56 and 60a (or between the surface 54 and labially occlusally facing surface 60*b* if the rotation is opposite) ensures that the wire cannot move beyond positions in which the foot portion is always poised and able to enter the slot as the bracket and arch wire rotate relative to one another toward the optimum position. Once there is some protrusion of some part of the arch wire foot portion into some part of the bracket slot they are able to perform even more positively a cooperative function of guiding the wire and the brackets in their relative movements toward the optimum position, this being facilitated by the rounded face 46. Owing intrinsically to the very small sizes to which it is possible to make the brackets of the invention it is found possible to function with relatively large angles of both tipping and rotation, for example, at least 75° in the case of tipping and at least 30° in the case of rotation. This aspect is also facilitated by the fact that, as explained below, the T-shape cross section wire is normally used after some initial correction has been achieved using round springy wires.

Any such misalignments between the arch wire and bracket slot cause the ligature loop 36 to be elastically deformed so that it applies the force F to the wire, which in the example illustrated by FIGS. 3 and 4, may be regarded as being applied at the junction of the wire labial and gingival faces 52 and 54. The reaction force R is applied at the line of contact of the wire occlusal lingual junction with the bracket labial surface part 26*b* to result in a couple tipping the bracket and the tooth as the ligature attempts to return to its shape of minimum strain. Similarly, if the bracket is rotated out of the optimum position as set by the wire fully inserted in the slot across its full width, as illustrated in broken lines in FIG. 13, then the ligature loop 36, or in this case both of the loops 36, will apply a restoring couple F' between the wire and the bracket.

Figure 5:
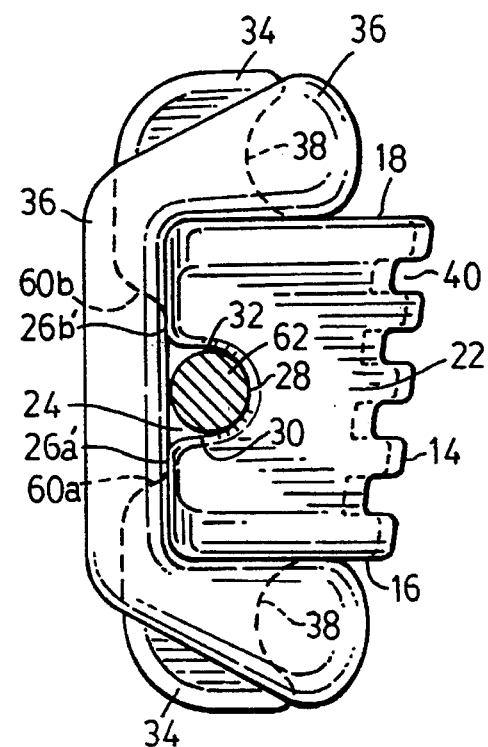
FIG. 5 is an end elevation similar to FIG. 2 and showing the the bracket of the invention in combination with a round cross section arch wire.

The surface 46 preferably is semi-circular to facilitate this guiding action, and also for ease of manufacture of the die used in production of the wire, although any contour that is convex toward the lingual and produces the same action can be employed. Preferably the bracket slot lingual surface 28 is also semi-circular, since this facilitates the use of the bracket with wires 62 of circular transverse cross-section, as illustrated by FIG. 5, when these are used in the preliminary stages of the procedures as described above. Thus, these round wires are urged by their own resilience, and also by the elastic ligature 36, to seek the bottom of the semi-circular slot labial wall 28, and in so doing apply the desired correcting forces to the bracket. It will be seen that the slot lingual surface 28 does not need to be struck about a mesial distal axis, but must be concave toward the labial and able to receive the circumference of the round cross section wire along a well defined mesially distally extending, gingivally occlusally located line. If this is the case the wire is able to apply its correcting force to the bracket more precisely in the gingival occlusal direction than is possible when the wire engages the flat gingivally occlusally extending lingual wall of a prior art square or rectangular bracket slot. An orthodontist who uses this procedure is already thoroughly familiar with the action of these round wires with rectangular slots, and will find the procedure is facilitated by use of the brackets of the invention, because of the more precise and effective interaction between the circular wire surface and the concave slot surface.

When the maximum alignment of the bracket slots along the wires has been achieved with round cross section wires, or at any other stage of the procedure deemed to be appropriate, the orthodontist may first employ a T-shape cross section wire of the invention of a material such as super- elastic nickel titanium which, because of its increased cross section, will usually be stiffer than the previously used wires. This first T-shape wire can be succeeded by one or more wires of progressively increasing stiffness such as of cobalt chromium material until the procedure is completed. It will be seen that the value of the force couple applied to the bracket is determined principally by the elastically deformed ligature urging the wire to move the foot portion into the slot until the fully butting contact of the cooperating surfaces is obtained, so that almost all of the propulsive forces are derived from the release of stored energy within the ligature. It is therefore relatively easy and efficient to choose the amount of force that is to be applied to an individual bracket by choice of the size and strength of the elastic ligature loop that is used. This must be contrasted with the prior art use of rectangular wires in rectangular slots, where it is often found that teeth already optimally aligned are subjected to spurious misaligning torques transmitted along the wires from the adjacent teeth by torsional deformation of the wire, these forces being difficult to control because of the need to positively engage the arch wire in the bracket slots and the relatively close spacing between adjacent brackets, especially if they are large, so that the torque or twisting in the wire occurs over very short lengths thereof. These can be avoided with the wires and brackets of the invention by ensuring that the ligatures used are not able to cause such torsional deformation. It is a rapid, simple procedure to change a ligature, which must usually be done in any case as the ligature ages and slackens in use, as compared to the changing of an arch wire. Moreover, very rigid wires can now be used in the final stages of the procedure, and it may be found possible to proceed directly from round wires to a single relatively rigid T-shape cross section wire, because they are not required to store and release strain energy for the correcting movements. The frictional forces which will be applied by the elastomeric ligatures against relative mesial or distal sliding between the wires and the brackets are inherently low, even though the ligatures are necessarily in constant contact with the wires, so that such sliding is not prevented, and will not involve the use of strong traction springs to overcome it, if some such sliding is required during the stages at which the T-shape cross section wire or wires are used.

The surfaces of orthodontic brackets may be polished as a stage of the bracket manufacture to minimize potential irritation to the interior of the patient's mouth and to the tongue. With the brackets and arch wires of the invention at least the labial surface portions 26*a*' and 26*b*' of the brackets preferably are polished to a so-called "mirror" finish with a surface roughness of less than 0.75 micrometer (30 microinch) with a preferred value of about 0.50 micrometer (20 microinch), while the lingual surface portions 58*a* and 58*b* of the wire crossbar preferably are polished to the same maximum value and with the same preferred value, so as to minimize friction that could hinder relative mesial distal sliding of the butting surfaces. For the same purpose the butting surfaces can each be provided with a very thin adherent coating, of the order of, or less than, 0.0025 mm (0.0001 in.) of a lower friction material such as polytetrafluoroethylene or titanium nitride.

Since the optimization is obtained by the butting engagement of only two surfaces very accurate expression of the programmed tooth attitude is obtained relative to the mesial distal axis of the arch wire slot, as compared to that obtained with rectangular wires in rectangular slots, owing as described above to the clearances that inherently must be provided to permit the rectangular wires to be inserted and to operate in the slots. Since in this attitude the foot portion will be centered in the slot along the full mesial distal width of the bracket close control is also obtained of the angulation about a labial lingual axis. However, since the principal function of the slot is to hold the bracket in the general area relative to the wire, the alignment system is able to permit a loose or large clearance fit between the lingually projecting wire foot and the slot, and permits the use of the highly rounded shape for the foot portion lingual wall to facilitate its insertion into the slot regardless of the amount of misalignment of the bracket slot from the optimized attitude relative to the mesial distal axis. The bracket slot should still be formed accurately so that it will function effectively with the earlier-used round wires to move the teeth as nearly as possible to the required height, leaving it to the T-shape cross section wire or wires primarily to take care of inclination (torque) and rotation about the mesial distal axis. With the teeth all at the same height it is not necessary for the T-shape cross section wires to be bent substantially out of the mesial distal plane, which means that a relatively stiff wire can be used without the danger of undesirably high forces being generated, and reducing the number of T-shape cross section wires that may need to be employed; it is contemplated that many procedures will require only the use of a single wire of the invention. It is therefore advantageous to manufacture at least the stiffer wires in a variety of different overall arch sizes so that the patients' arch dimension size can be harmonized with the patients' bone structure.

It will be seen from a comparison of FIGS. 3 and 4 that as the bracket rotates relative to the wire, and the wire foot portion protrudes further into the slot, the distance N which is the length of the lever arm between the opposing forces F and R increases, so that the decrease in the force F as the ligature becomes more relaxed is compensated to give a more constant torque couple, and one that may even increase. It is therefore possible to establish a range of values for brackets, wires and ligatures within which near-optimal torque couples can be sustained throughout the procedure for maximum efficiency in corrective movement with good tissue response and avoidance of undesired side effects, such as tissue damage and root resorbtion. Owing to the individual force adjustment that can be made for each bracket it is possible to refine this adjustment to take account of the root length of each tooth, and the torque that is therefore required to optimize the speed at which it can be tipped about the mesial distal axis.

It is a fundamental objective with orthodontic procedures that they proceed as rapidly as possible, consistent with the avoidance of the above described undesired side effects. Orthodontic procedures are only possible because the teeth are securely anchored in the bone of the jaw to the extent that they withstand without movement the surprisingly high impact forces to which they are subjected in normal operation, and yet they can be moved in that bone while remaining securely attached by the persistent application of relatively extremely small forces. This desired movement in the bone takes place by means of a relatively complex process involving special cells which absorb bone at the positive pressure site (Osteoclasts), and which deposit bone (Osteoblasts) at the opposite negative pressure site, the process requiring a minimum or threshold amount of force for it to become established. The tissue and bone of the jaw have a generous blood supply and this should be maintained at as normal a level as possible to maintain the cells healthy and active and thus facilitate this cellular action; an adequate blood supply is also needed to maintain the surrounding supporting tissue in healthy condition. There is therefore a specific predeterminable range of force that should be employed, namely sufficient to ensure the cellular action takes place, while not so large that the blood supply is reduced, and it is found that in practice the force required is comparatively relatively low. It is difficult in practice to give numerical values to these forces, since the application will vary from tooth to tooth in the same mouth, but it is known that they are considerably smaller than those which are encountered in convential edgewise procedures. High forces do not therefore necessarily result in faster movement of the teeth, and can instead result in even slower movement because of the resultant restriction of the blood supply and consequent inhibition of the entire process; there is also as described above the increased possibility of damage to or even death of the tissue and the teeth roots and permanent resorption of the bone of the jaw.

Prior processes that rely principally upon the elasticity and deformation of the wires to rotate the brackets about the mesial distal axis present two difficult problems. Firstly that the forces applied tend initially to be quite high, to the extent that they may in fact inhibit the movement process, and secondly that they tend to decrease quite rapidly as the brackets move owing to the short elastic range of movement involved, the slow tooth movement because of the process inhibition tending to disguise the rapid force reduction, which of course eventually results in the wire becoming ineffective because the applied force has dropped below the threshold value. The optimum procedures are therefore those in which light moving couples within a narrow range above the threshold value are applied as persistently as possible and, as indicated above, such procedures are readily established with the brackets and arch wires of the invention.

Figure 6:
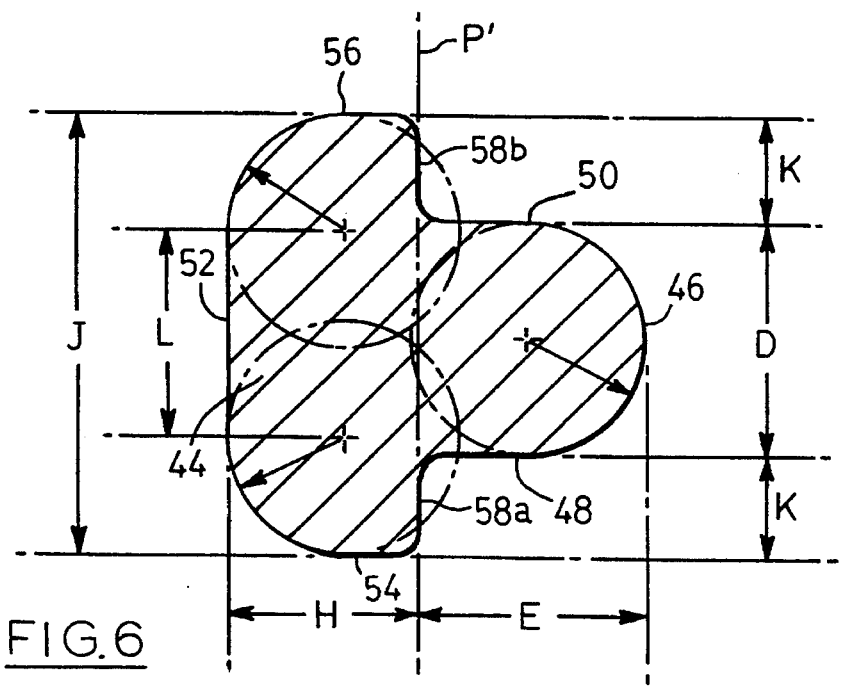
FIG. 6 is a transverse cross section through an arch wire of the invention in a transverse gingival occlusal plane to permit description of critical parameters and dimensions thereof, and to illustrate the development of a die suitable for its manufacture.

FIG. 6 illustrates a preferred cross-section for the arch wire of the invention, and also illustrates how a suitable die for the production of the wire by drawing or rolling can be developed. As described above, it is preferred that the wire lingual surface 46 be semi-circular and its diameter is given the reference D. Since the bracket slot preferably is shaped to receive round wires it is preferred that the labial lingual dimension E of the wire foot portion be just less than the value D, so that when the foot portion is fully within the slot there is the above-mentioned generous clearance. The labial lingual dimension H and the gingival occlusal dimension J of the crossbar portion are not critical, provided that the gingival occlusal dimension K of each lingual surface part 58a and 58b is adequate for its purpose and the wire cross section contains enough material to give the desired effect. For patient comfort the two labially-facing junctions between the surfaces 52 and 54, and 52 and 56, are quarter circles of the same diameter as that of the surface 46, struck about centres spaced apart a distance L. The remaining convex junctions are rounded to avoid sharp edges.

In a particular arch wire embodiment for use with a bracket having a slot 24 of 0.55 mm (0.022 in) gingival occlusal dimension and of 0.525 mm (0.021 in) labial lingual dimension the value of D is 0.5 mm (0.020 in) and the value of E is 0.475 mm (0.019 in.) with a preferred tolerance for both of ±0.0125 mm (0.0005 in), since these are dimensions which are critical to obtain the desired function. For this embodiment the value of H is 0.4 mm (0.016 in.), the value of K is 0.225 mm (0.009 in.), that of J is 0.90 mm (0.036 in.) and that of L is 0.437 mm (0.0175 in.).

For some procedures, such as those which involve mainly retraction of the incisors without the need to tip them substantially, it is possible and may be preferred to use a composite arch wire in which only the mesial or central portion extending over the central and lateral incisors is of T-shape cross section, while the distal end portions extending over the canines, bicuspids and molars are of circular transverse cross section.

Figure 7:
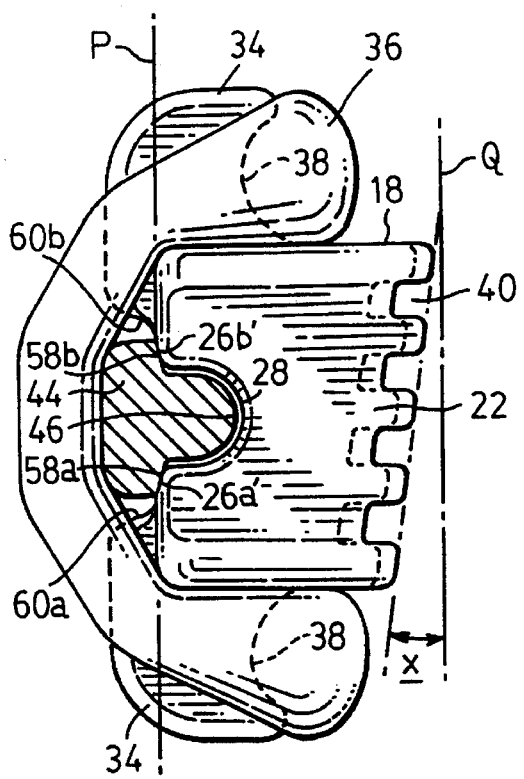
FIGS. 7 and 8 are end elevations of brackets which are respectively other and further embodiments of the invention.
Figure 8:
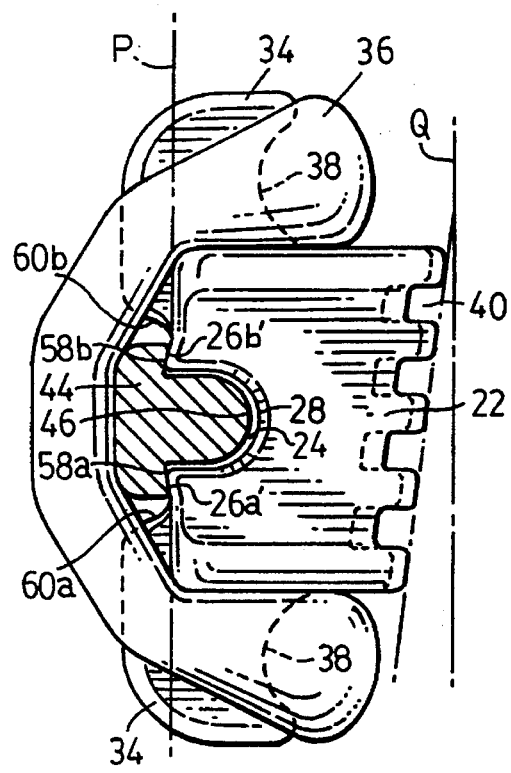

In the embodiment of FIGS. 1–5 the bracket labial surface portions 26a and 26b, and the slot bordering parts 26a' and 26b', are all flat and coplanar, and this is to be preferred for ease of manufacture of the brackets and of the arch wires to the necessary precise dimensions, especially in view of the small values involved. However, this coplanar structure is not necessary for successful operation of the invention, and FIGS. 7 and 8 illustrate respective embodiments that are variants on the embodiment of FIGS. 1–5, and in which this is not the case. Thus in the embodiment of FIG. 7 the slot bordering parts 26a' and 26b' are inclined toward the labial as they extend respectively toward the occlusal (part 26a') and toward the gingival (part 26b'), so that the slot has an inwardly tapering portion and the corresponding junctions are obtuse angled, while the wire has the surfaces 58a and 58b correspondingly inclined in the labial direction from the gingival and occlusal surfaces of the crossbar portion to the corresponding surfaces of the foot portion, so that again the junctions are obtuse angled. In the other embodiment of FIG. 8 the slot bordering parts are inclined toward the lingual to form acute angled junctions, while the wire surfaces 58a and 58b are correspondingly inclined toward the lingual to form acute angled junctions; the resulting slot edges are rounded to avoid production of sharp edges. In both embodiments the cooperative action of the wire and the bracket under the urge of the wire resilience and that of the ligation loop is the same as with the embodiment of FIGS. 1 to 5, and will result in the bracket being brought to the desired optimum attitude relative to the wire, whereupon there will be maximum butting contact between the slot border parts and the corresponding wire surfaces.

Figure 9:
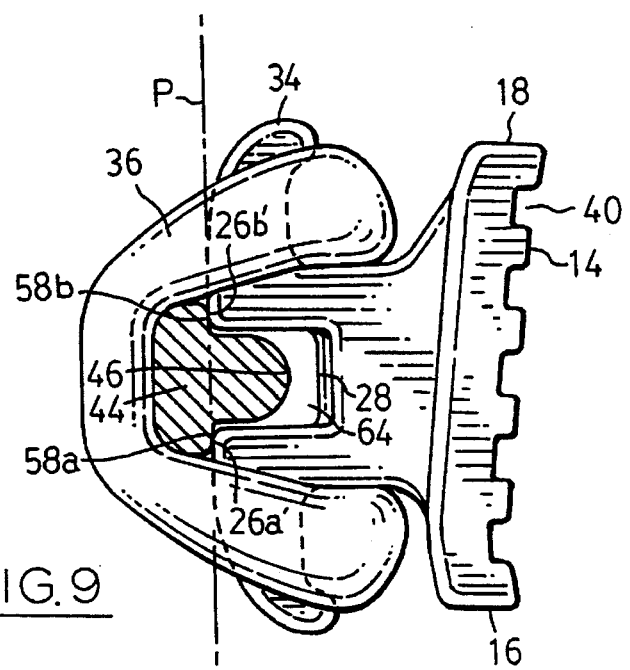
FIG. 9 is an end elevation similar to FIG. 2 of a bracket structure in which the arch wire slot is of rectangular cross section, permitting its use with wires of square and rectangular cross section, as well as the T-shape cross section wires of the invention.

FIG. 9 illustrates a bracket structure provided with a mesial distal slot 64 of rectangular cross section in the gingival occlusal plane, so that in that respect it corresponds to the known rectangular slot brackets. The bracket is made with flat coplanar slot bordering surfaces 24a' and 24b' as with the embodiment of FIGS. 1–5, or with inclined slot bordering surfaces, as with the embodiments of FIGS. 7 and 8, for butting cooperation with the surfaces 58a and 58b of the wire 44, so that it cooperates with this bracket as with the previously described embodiments with the T-shape cross section wire. The bracket will also cooperate with round cross section wires but not as effectively and accurately as the brackets of the invention in which the slot lingual surface is also highly rounded, and preferably is semi-circular.

Figure 10:
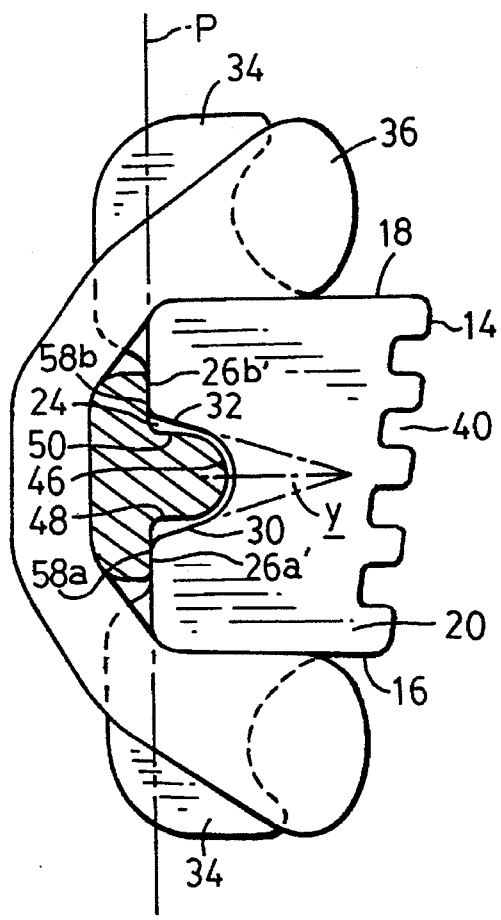
FIG. 10 is an end elevation of a bracket which is a still further embodiment, in which the slot gingival and occlusal surfaces diverge away from one another toward the labial.
Figure 11:
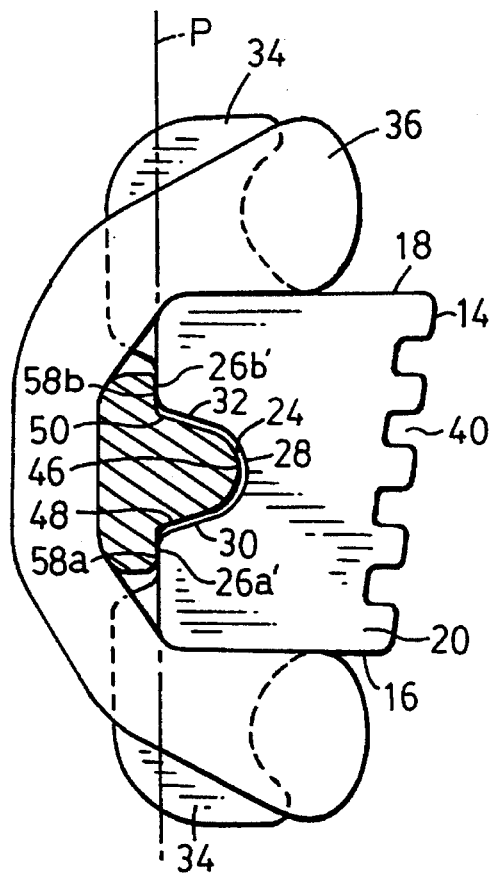
FIG. 11 is an end elevation of the bracket of FIG. 10, showing in combination therewith a T-shape cross section arch wire which is another embodiment of the invention.

In the embodiments of FIGS. 10 and 11 the slot 24 is formed with its gingival and occlusal surfaces 30 and 32 diverging gingivally and occlusally respectively at an angle y toward the labial, the slot junctions and the labial surface parts 26a' and 26b' thereby being spaced further apart than in the previously described embodiments; the arch wire used with such a bracket has greater crossbar dimensions J and L to permit it to bridge the wide slot mouth and still provide slot edge bearing surfaces 58a and 58b of adequate gingival occlusal depth for engagement with the bracket surfaces 26a' and 26b'. Brackets having arch wire slots of this shape are also able to cooperate with arch wires of half square, half round (D-shape) transverse cross section in the performance of orthodontic procedures; such brackets and arch wires are more specifically disclosed and claimed in my copending U.S. application Ser. No. 07/826,737, filed 28 Jan., 1992, now U.S. Pat. No. 5,224,858, the disclosure of which is incorporated herein by this reference. FIG. 11 illustrates a different embodiment of the arch wire in which the foot portion gingival and occlusal surfaces 54 and 56 are inclined toward one another from the labial toward the lingual, so that the cross section of the foot portion conforms more closely to that of the slot, thereby providing somewhat more precise guidance as the foot portion enters the slot. In both embodiments it is preferred that the angle y not be quite as large as the preferred maximum value of 25° (preferred range of 5° to 25°) disclosed in my prior application, in order to maintain the gingival occlusal dimension of the bracket body as small as possible, and a smaller maximum value of 20° is preferred.

Figure 12:
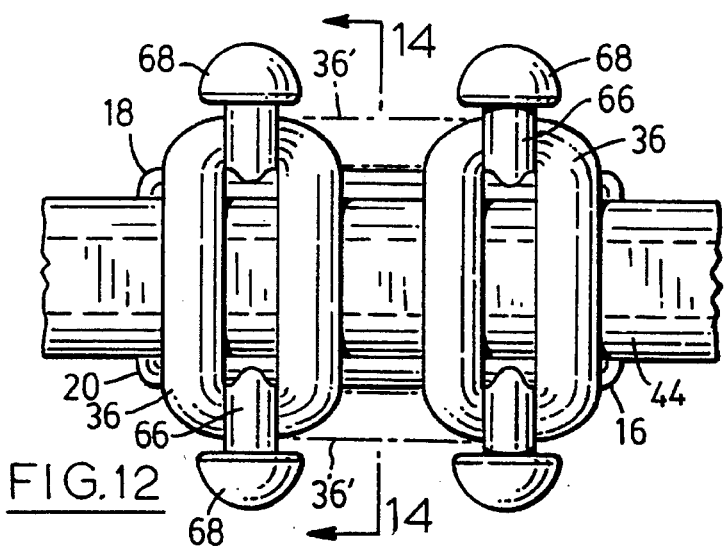
FIG. 12 is an elevation from the labial of a bracket which is a further embodiment, in which headed posts are used in place of tie wings for retention of an elastomeric ligation loop.
Figure 13:
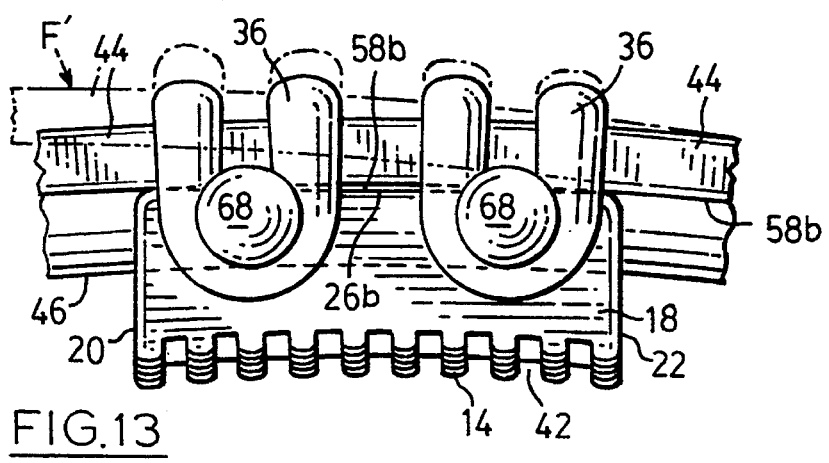
FIG. 13 is a plan view from the gingival or occlusal of the bracket of FIG. 12.
Figure 14:
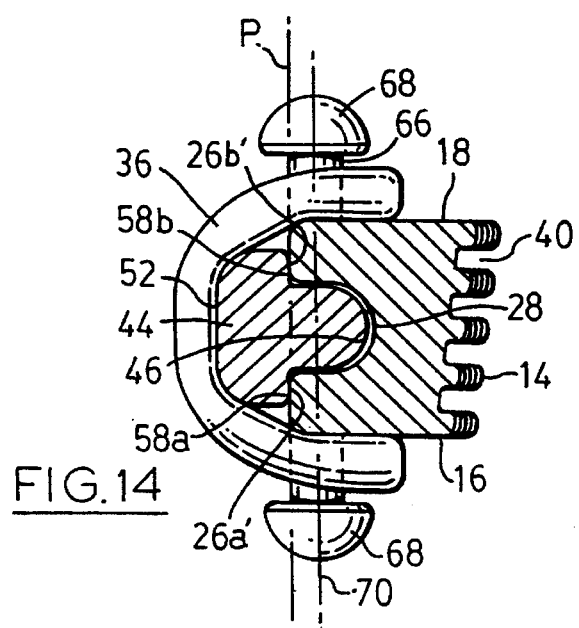
FIG. 14 is a transverse cross section of the bracket of FIGS. 12 and 13 on the line 14—14 of FIG. 12.

FIGS. 12–17 illustrate other brackets of the invention for use with the arch wires of the invention, in which the tie wings 34 of the previously described embodiments are replaced by at least one pair of coaxial gingivally and occlusally extending cylindrical posts 66, each post being provided with an enlarged head 68 which assists in retaining the ligature 36 on the posts. The embodiment illustrated by FIGS. 12–14 is provided with two such pairs of posts spaced mesially distally from one another, so that the bracket is able to provide better control of tooth rotation about the gingival occlusal axis. This embodiment also provides further choice of the value of the force that is applied by the elastic ligature 36 by choice of the pair of posts around which the ligature is trained, if only a single ligature is used, or by use of a single ligature 36' that is entrained around all four posts, as indicated in broken lines in FIG. 12, or as illustrated by use of two separate ligatures each trained about a respective pair of posts.

In the last described embodiment the posts 66 are disposed so that the most labially disposed portion of its cylindrical surface is in the plane P (FIG. 14) containing the butting cooperating bracket and wire surfaces, and the coaxial post axes 70 are parallel to the plane P, this having the advantage that the labial lingual dimension can be kept small while providing adequate lingual space behind the posts for the ligature loop. In the embodiment of FIG. 15 these axes 70 are instead parallel to the inclined lingual bracket surface 14 and are disposed more toward the lingual. The latter structure is used particularly on the canine teeth of patients who are prone to irritation caused by mechanical contact between the bracket and the mouth lining.

In the bracket of FIG. 16 the posts 66 are cranked labially along their length so that they protrude labially beyond the labial surface portions 26a and 26b of the bracket body, in a preferred embodiment by as much as 0.2 mm (0.008 in), and therefore are also able to provide the mesially distally extending stop surfaces 60a and 60b for cooperation with the arch wire in the extreme rotated position, while the bracket of FIG. 17 retains the relative positioning of the bracket of FIG. 14 of the plane P and the post axes 70 and has separate labially extending protrusions 72 which provide the stop surfaces 60a and 60b.

The brackets of FIGS. 1–5 and 7–11 are particularly suited for manufacture from transparent crystalline materials, such as α-alumina, while those of FIGS. 12–17 are particularly suited for manufacture from metal, particularly by metal casting techniques.

I claim:

1. An orthodontic arch wire for use in combination with an orthodontic bracket comprising a bracket body having labial, lingual, gingival, occlusal, mesial and distal surfaces, and having a mesial distal extending arch wire slot opening at the bracket labial surface, the bracket labial surface being divided by the slot to have two labial slot border surface parts on respective sides of the slot;

the arch wire being of T-shape cross section in a gingival occlusal transverse plane, comprising a labial lingual extending foot portion having lingual, gingival and occlusal surfaces and a gingival occlusal extending crossbar portion having labial, gingival and occlusal surfaces and also having two spaced lingual surface parts that have respective mesial distal extending junctions with the gingival and occlusal surfaces of the foot portion;

wherein the gingival occlusal height of the foot portion is smaller than the corresponding height of the bracket slot for the foot portion to be insertable into the bracket slot with clearance between the foot portion gingival and occlusal surfaces and the corresponding adjacent slot gingival and occlusal surfaces;

wherein the lingual surface of the foot portion is convex toward the lingual and is rounded in the gingival occlusal transverse plane; and wherein the gingival occlusal height of the crossbar portion is greater than the corresponding height of the bracket slot, whereby the two spaced crossbar lingual surface parts butt against the two respective bracket labial slot border surface parts when the foot portion is fully inserted into the slot and thereby establish the position and the attitude of the wire and the bracket relative to one another.

2. An arch wire as claimed in claim 1, wherein the labial lingual depth of the foot portion is approximately equal to the gingival occlusal height thereof.

3. An arch wire as claimed in claim 1, wherein the lingual surface of the foot portion is semi-circular about a mesial distal axis in the gingival occlusal transverse plane.

4. An arch wire as claimed in claim 1, wherein the gingival and occlusal surfaces of the foot portion are parallel to one another.

5. An arch wire as claimed in claim 1, wherein the gingival and occlusal surfaces of the foot portion diverge away from one another from the lingual toward the labial.

6. An arch wire as claimed in claim 1, wherein the two crossbar portion lingual surface parts are coplanar and both have right angle junctions with the respective gingival and occlusal surfaces of the foot portion.

7. An arch wire as claimed in claim 1, wherein the two crossbar portion lingual surface parts both have obtuse angle junctions with the respective gingival and occlusal surfaces of the foot portion.

8. An arch wire as claimed in claim 1, wherein the two crossbar portion lingual surface parts both have acute angle junctions with the respective gingival and occlusal surfaces of the foot portion.

9. An arch wire as claimed in claim 1, wherein the two crossbar portion lingual surface parts have a mirror surface finish of roughness not more than 0.75 micrometer (30 microinch).

10. An arch wire as claimed in claim 1, wherein the two crossbar portion lingual surface parts have thereon a coating of a lower friction material.

11. The combination of an arch wire, an orthodontic bracket cooperating therewith, and ligating means on the bracket body engageable with the labial face of the arch wire to maintain the bracket and the arch wire in cooperative engagement with one another;

the bracket comprising a bracket body having labial, lingual, gingival, occlusal, mesial and distal surfaces, and having a mesial distal extending arch wire slot opening at the bracket labial surface;

the bracket labial surface being divided by the slot to have two labial slot border surface parts on respective sides of the slot;

the arch wire being of T-shape cross section in a gingival occlusal transverse plane, comprising a labial lingual extending foot portion having lingual, gingival and occlusal surfaces and a gingival occlusal extending crossbar portion having labial, gingival and occlusal surfaces and also having two spaced lingual surface parts that have respective mesial distal extending junctions with the gingival and occlusal surfaces of the foot portion;

wherein the gingival occlusal height of the foot portion is smaller than the corresponding height of the bracket slot for the foot portion to be insertable into the bracket slot with clearance between the foot portion gingival and occlusal surfaces and the corresponding adjacent slot gingival and occlusal surfaces;

wherein the lingual surface of the foot portion is convex toward the lingual and is rounded in the gingival occlusal transverse plane;

wherein the gingival occlusal height of the crossbar portion is greater than the corresponding height of the bracket slot, whereby the two spaced crossbar lingual surface parts butt against the two respective bracket labial slot border surface parts when the foot portion is fully inserted into the slot to thereby establish an optimum position and attitude of the wire and the bracket relative to one another;

wherein with the bracket and the arch wire not in the optimum position and attitude relative to one another the foot portion can protrude into the slot to maintain the bracket and the arch wire in cooperative engagement with one another, and movement of the foot portion into the slot guides the bracket and the arch wire toward the optimum position and attitude; and wherein the ligating means urge the arch wire lingually to move the foot portion fully into the slot for said butting engagement of both of the crossbar lingual surface parts with both of the respective bracket labial slot border surface parts.

12. A combination as claimed in claim 11, wherein the slot lingual surface is concave toward the labial in a gingival occlusal transverse plane.

13. A combination as claimed in claim 12, wherein the slot lingual surface is semi-circular in the gingival occlusal transverse plane.

14. A combination as claimed in claim 13, wherein the slot mesially and distally extending gingival and occlusal surfaces are parallel to one another.

15. A combination as claimed in claim 11, wherein the two arch wire crossbar portion lingual surface parts are coplanar and both have right angle junctions with the respective gingival and occlusal surfaces of the foot portion, and the two bracket labial slot border surface parts that are butted by the crossbar portion lingual surface parts are flat and coplanar with one another.

16. A combination as claimed in claim 11, wherein the two arch wire crossbar portion lingual surface parts both have obtuse angle junctions with the respective gingival and occlusal surfaces of the foot portion, and wherein the two labial bracket slot border surface parts that are butted by the crossbar portion lingual surface parts are inclined labially from their junctions with the slot edges, so that the said junctions are also obtuse angled.

17. A combination as claimed in claim 11, wherein the two arch wire crossbar portion lingual surface parts both have acute angle junctions with the respective gingival and occlusal surfaces of the foot portion, and wherein the two labial bracket slot border surface parts that are butted by the crossbar portion lingual surface parts are inclined lingually from their junctions with the slot edges, so that the said junctions are also acute angled.

18. A combination as claimed in claim 11, wherein the two bracket labial slot border surface parts have a mirror surface finish of roughness not more than 0.75 micrometer (30 microinch).

19. A combination claimed in claim 11, wherein the two bracket labial slot border surface parts have thereon a coating of a lower friction material.

20. A combination as claimed in claim 11, wherein the bracket body is provided beyond the respective labial slot border labial surface parts with two labially gingivally and labially occlusally facing mesially distally extending stop surfaces on each side of the slot protruding labially beyond the respective labial slot border surface parts, a respective stop surface being engaged by the arch wire upon a predetermined relative rotation of the bracket and the arch wire from the optimum attitude about a mesial distal extending axis.

21. A combination as claimed in claim 11, wherein the bracket body is provided with gingivally occlusally extending tie wings for reception of an elastomeric ligature for retaining the arch wire in the slot.

22. A combination as claimed in claim 21, wherein the tie wings protrude labially beyond the respective labial slot border surface parts to provide respective labially gingivally and labially occlusally facing mesially distally extending stop surfaces engaged by the arch wire upon a predetermined relative rotation of the bracket and the arch wire from the optimum attitude about a mesial distal extending axis.

23. A combination as claimed in claim 11, wherein the bracket body is provided with a pair of gingivally occlusally extending headed posts for reception of an elastomeric ligature for retaining an arch wire in the slot.

24. A combination as claimed in claim 23, wherein the posts protrude labially beyond the respective labial slot border surface parts to provide respective labially gingivally and labially occlusally facing mesially distally extending stop surfaces engaged by the arch wire upon a predetermined relative rotation of the bracket and the arch wire from the optimum attitude about a mesial distal extending axis.

25. A combination as claimed in claim 23, wherein the bracket body is provided with two mesial distal extending labial protrusions at respective edges of the labial slot border surface parts, the protrusions protruding labially beyond the respective labial slot border surface parts to provide respective labially gingivally and labially occlusally facing mesially distally extending stop surfaces engaged by the arch wire upon a predetermined relative rotation of the bracket and the arch wire from the optimum attitude about a mesial distal extending axis.

26. A combination as claimed in claim 23, wherein the bracket body is provided with two mesially distally spaced gingivally occlusally extending pairs of headed posts, each for reception of a ligature for retaining an arch wire in the slot.

27. A combination as claimed in claim 11, wherein the bracket body is provided with two mesially distally spaced gingivally occlusally extending pairs of headed posts, each for reception of an elastomeric ligature for retaining the arch wire in the slot.

28. A combination as claimed in claim 11, wherein the slot mesially and distally extending gingival and occlusal surfaces diverge away from one another from the lingual toward the labial.

29. The combination of an orthodontic bracket and an arch wire cooperating therewith;

wherein the bracket comprises a bracket body having labial, lingual, gingival, occlusal, mesial and distal surfaces, and having a mesial distal extending arch wire slot opening at the bracket labial surface;

the bracket labial surface being divided by the slot to have two labial slot border surface parts on respective sides of the slot;

the arch wire being of T-shape cross section in a gingival occlusal transverse plane, comprising a labial lingual extending foot portion having lingual, gingival and occlusal surfaces and a gingival occlusal extending crossbar portion having labial, gingival and occlusal surfaces and also having two spaced lingual surface parts that have respective mesial distal extending junctions with the gingival and occlusal surfaces of the foot portion;

wherein the gingival occlusal height of the foot portion is smaller than the corresponding height of the bracket slot for the foot portion to be insertable into the bracket slot with clearance between the foot portion gingival and occlusal surfaces and the corresponding adjacent slot gingival and occlusal surfaces;

wherein the lingual surface of the foot portion is convex toward the lingual and is rounded in the gingival occlusal transverse plane;

wherein the gingival occlusal height of the crossbar portion is greater than the corresponding height of the bracket slot, whereby the two spaced crossbar lingual surface parts butt against the two respective bracket labial slot border surface parts when the foot portion is fully inserted into the slot to thereby establish an optimum position and attitude of the wire and the bracket relative to one another; and wherein with the bracket and the arch wire not in the optimum position and attitude relative to one another the foot portion can protrude into the slot to maintain the bracket and the arch wire in cooperative engagement with one another, and movement of the foot portion lingually into the slot under the urge of a ligating means on the bracket guides the bracket and the arch wire toward the optimum position and attitude.

30. A combination as claimed in claim 29, wherein the slot lingual surface is concave toward the labial in a gingival occlusal transverse plane.

31. A combination as claimed in claim 30, wherein the slot lingual surface is semi-circular in the gingival occlusal transverse plane.

32. A combination as claimed in claim 29, wherein the slot mesially and distally extending gingival and occlusal surfaces are parallel to one another.

33. A combination as claimed in claim 29, wherein the two arch wire crossbar portion lingual surface parts are coplanar and both have right angle junctions with the respective gingival and occlusal surfaces of the foot portion, and the two bracket labial slot border surface parts that are butted by the crossbar portion lingual surface parts are flat and coplanar with one another.

34. A combination as claimed in claim 29, wherein the two arch wire crossbar portion lingual surface parts both have obtuse angle junctions with the respective gingival and occlusal surfaces of the foot portion, and wherein the two labial bracket slot border surface parts that are butted by the crossbar portion lingual surface parts are inclined labially from their junctions with the slot edges, so that the said junctions are also obtuse angled.

35. A combination as claimed in claim 29, wherein the two arch wire crossbar portion lingual surface parts both have acute angle junctions with the respective gingival occlusal surfaces of the foot portion, and wherein the two labial bracket slot border surface parts that are butted by the crossbar portion lingual surface parts are inclined lingually from their junctions with the slot edges, so that the said junctions are also acute angled.

36. A combination as claimed in claim 29, wherein the two arch wire crossbar portion lingual surface parts and the two bracket labial slot border surface parts both have a mirror surface finish of roughness not more than 0.75 micrometer (30 microinch).

37. A combination as claimed in claim 29, wherein the two arch wire crossbar portion lingual surface parts and the two bracket labial slot border surface parts both have thereon a coating of a lower friction material.

38. A combination as claimed in claim 29, wherein the bracket body is provided with two mesial distal extending labial protrusions at respective edges of the labial slot border surface parts, the protrusions protruding labially beyond the respective labial slot border surface parts to provide respective labially gingivally and labially occlusally facing mesially distally extending stop surfaces engaged by the arch wire upon a predetermined relative rotation of the bracket and the arch wire from the optimum attitude about a mesial distal extending axis.

39. A combination as claimed in claim 29, wherein the bracket body is provided with gingivally occlusally extending tie wings for reception of an elastomeric ligature for retaining the arch wire in the slot.

40. A combination as claimed in claim 39, wherein the tie wings protrude labially beyond the respective labial slot border surface parts to provide respective labially gingivally and labially occlusally facing mesially distally extending stop surfaces engaged by the arch wire upon a predetermined relative rotation of the bracket and the arch wire from the optimum attitude about a mesial distal extending axis.

41. A combination as claimed in claim 29, wherein the bracket body is provided with a pair of gingivally occlusally extending headed posts for reception of an elastomeric ligature for retaining the arch wire in the slot.

42. A combination as claimed in claim 41, wherein the posts protrude labially beyond the respective labial slot border surface parts to provide respective labially gingivally and labially occlusally facing mesially distally extending stop surfaces engaged by the arch wire upon a predetermined relative rotation of the bracket and the arch wire from the optimum attitude about a mesial distal extending axis.

43. A combination as claimed in claim 29, wherein the bracket body is provided with two mesial distal extending labial protrusions at respective edges of the labial slot border surface parts, the protrusions protruding labially beyond the respective labial slot border surface parts to provide respective labially gingivally and labially occlusally facing mesially distally extending stop surfaces for engagement by the arch wire upon a predetermined relative rotation of the bracket and the arch wire from the optimum attitude about a mesial distal extending axis.

44. A combination as claimed in claim 29, wherein the slot mesially and distally extending gingival and occlusal surfaces diverge away from one another from the lingual toward the labial.

* * * * *